United States Patent [19]

Trout, III

[11] Patent Number: 5,207,695

[45] Date of Patent: May 4, 1993

[54] AORTIC GRAFT, IMPLANTATION DEVICE, AND METHOD FOR REPAIRING AORTIC ANEURYSM

[76] Inventor: Hugh H. Trout, III, 3037 Ordway St., NW., Washington, D.C. 20008

[21] Appl. No.: 787,731

[22] Filed: Nov. 4, 1991

Related U.S. Application Data

[63] Continuation of Ser. No. 367,716, Jun. 19, 1989, abandoned.

[51] Int. Cl.⁵ .......................... A61F 2/06; A61F 2/04; A61B 17/08
[52] U.S. Cl. .................................. 606/153; 606/198; 606/191; 623/1; 600/36
[58] Field of Search ....................... 623/1, 12; 606/153, 606/191, 198, 200; 600/36, 37

[56] References Cited

U.S. PATENT DOCUMENTS

| | | | |
|---|---|---|---|
| 3,166,072 | 1/1965 | Sullivan, Jr. | 606/153 |
| 3,815,578 | 6/1975 | Bucalo | 606/153 |
| 4,392,857 | 7/1983 | Beran | 604/179 |
| 4,562,596 | 1/1986 | Kornberg | 623/1 |
| 4,643,184 | 2/1987 | Mobin-Uddin | 606/198 |
| 4,681,110 | 7/1987 | Wiktor | 128/343 |
| 4,693,249 | 9/1987 | Schenck et al. | 128/334 R |
| 4,740,207 | 4/1988 | Kreamer | 623/1 |
| 4,787,899 | 11/1988 | Lazarus | 623/1 |
| 4,793,348 | 12/1988 | Palmaz | 128/325 |
| 4,872,874 | 10/1989 | Taheri | 623/1 |
| 5,007,926 | 4/1991 | Derbyshire | 623/1 |
| 5,104,399 | 4/1992 | Lazarus | 623/1 |

Primary Examiner—Paul Prebilic
Attorney, Agent, or Firm—Patrick J. Coyne; Kenneth M. Massaroni

[57] ABSTRACT

An aortic graft and system and method for implanting the aortic graft are provided. The aortic graft comprises a substantially cylindrical graft material with attachment means which comprise a plurality of post and hook assemblies which are implanted with a double catheter system to penetrate the aorta wall above and below the aneurysm to provide firm attachment of the aortic graft and, thereby, exclude the aneurysm from the circulatory system.

17 Claims, 7 Drawing Sheets

AORTIC GRAFT, IMPLANTATION DEVICE, AND METHOD FOR REPAIRING AORTIC ANEURYSM

This application is a continuation of application Ser. No. 07/367,716 filed Jun. 19, 1989, now abandoned.

The invention is an aortic graft, and a device and method of using that device for repair and treatment of arterial aortic aneurysms. An aneurysm is a ballooning of the wall of an artery resulting from the weakening of the artery due to disease or other conditions. Left untreated, the aneurysm will frequently rupture resulting in loss of blood through the rupture.

Aortic aneurysms are the most common form of arterial aneurysm and are life threatening. The aorta is the main artery which supplies blood to the circulatory system. The aorta arises from the left ventricle of the heart, passing upward and bending over behind the heart and passing down through the thorax and abdomen. The abdominal aorta supplies two side vessels to the kidneys, the renal arteries. Below the level of the renal arteries, the abdominal aorta continues to about the level of the fourth lumbar vertebrae where it divides into the iliac arteries. The iliac arteries, in turn, supply blood to the lower extremities and perineal region.

It is common for an aortic aneurysm to occur in that portion of the abdominal aorta between the renal arteries and the iliac arteries. This portion of the abdominal aorta is particularly susceptible to weakening, resulting in an aortic aneurysm. An aortic aneurysm larger than about 4 cm. in diameter in this section of the aorta is ominous. Left untreated, the aneurysm may rupture, resulting in rapid and usually fatal hemorrhaging.

Aneurysms in the abdominal aorta are associated with a particularly high mortality rate. Accordingly, current medical standards call for urgent operative repair of abdominal aortic aneurysms. Abdominal surgery itself is a major procedure resulting in substantial stress to the body. Although the mortality rate for an aortic aneurysm is extremely high, there is also considerable mortality and morbibity associated with surgical intervention to repair an aortic aneurysm. This intervention involves going through the abdominal wall to the location of the aneurysm to bypass or replace the diseased section of the aorta at the aneurysm. A prosthetic device, typically a synthetic tube, is used for this purpose. This graft serves to exclude the aneurysm from the circulatory system, thus relieving pressure and stress on the weakened section of the aorta at the aneurysm.

Repair of an aortic aneurysm by surgical means is a major operative procedure. In addition, substantial morbidity accompanies the procedure, resulting in a protracted recovery period. Finally, the procedure entails a substantial risk of mortality. While surgical intervention is nonetheless called for in the case of an aortic aneurysm in spite of these risks, certain patients may not be able to tolerate the stress of intraabdominal surgery. It is desirable to reduce the mortality and morbidity associated with intraabdominal surgical intervention.

In recent years, methods have been developed to attempt to treat an aortic aneurysm without the attendant risks of intraabdominal surgical intervention. Among them are inventions disclosed and claimed in Kornberg, U.S. Pat. No. 4,562,596 (Jan. 7, 1986) for Aortic Graft, Device and Method for Performing an Intraluminal Abdominal Aortic Aneurysm Repair; and Lazarus, U.S. Pat. No. 4,787,899 (Nov. 29, 1988) for Intraluminal Graft Device, System and Method.

Kornberg discloses an aortic graft comprising a flexible tubular material having a plurality of struts to lend the graft stability and resiliency. The struts have angled hooks with barbs at their upper ends which are securely attached to the inside of the aorta above the aneurysm. Kornberg's graft is inserted using a tubular device also disclosed in his patent.

Kornberg, however, anchors only the proximal end of the graft in the aorta. Kornberg claims that the downward flow of blood holds the distal graft securely in place so that no mechanical attachment is necessary distally. Kornberg, U.S. Pat. No. 4,562,596, Col. 6, lines 24–27. The blood pressure in the abdominal aorta, however, is typically in the magnitude of 130 mm of mercury. In spite of the direction of flow of blood through the graft, proximal to distal, substantial back pressures within the aneurysm will result unless the distal end is also mechanically attached. Without distal attachment, the device of Kornberg will not effectively exclude the weakened arterial wall at the site of the aneurysm from the forces and stress associated with the blood pressure.

Lazarus discloses a grafting system that employs a plurality of staples mounted in the proximal end of the graft. Lazarus's staples are forced through the aorta wall by means of a balloon catheter. As does Kornberg, however, Lazarus discloses staples mounted only in the proximal end of the graft. There is no teaching or suggestion in Lazarus, U.S. Pat. No. 4,787,899 as to the desirability or means for mechanically attaching the graft to the distal aorta below the level of the aneurysm.

Lazarus, U.S. Pat. No. 4,787,899 also discloses various means for repairing the aorta. Among them are surgical techniques, the use of nitinol coil, and various graft systems that are implaced by the use of a balloon catheter system.

Hence, although in recent years certain techniques have been developed that avoid or reduce the stress, morbidity, and risk of mortality associated with surgical intervention to repair aortic aneurysms, the systems that have been developed do not effectively treat the aneurysm and exclude the affected section of aorta from the pressures and stresses associated with the circulation. None of the devices disclosed in the prior art provide a reliable and quick means to bypass an aneurysmal artery.

It is therefore an object of the invention to provide a method to repair an aortic aneurysm with a much lower risk of morbidity and mortality than that associated with intraabdominal surgical repair of the aneurysm.

A further object of the invention is to provide a means for repairing an aortic aneurysm in patients who cannot tolerate major abdominal surgery.

A further object of the invention is to reduce the risk of morbidity and mortality associated with extensive surgical procedures.

Another object of the invention is to provide a means to quickly stabilize patients suffering from an aortic aneurysm as an emergency procedure.

Yet a further object of the invention is to provide a means for treatment of abdominal aortic aneurysm without major surgical intervention.

A further object of the invention is to provide a device for repair of abdominal aortic aneurysms while reducing the morbidity and mortality associated with surgical procedures for repair of abdominal aortic aneurysms.

An additional object of the invention is to provide a procedure and system for repairing abdominal aortic aneurysms at greatly reduced cost in terms of medical resources relative to intraabdominal surgical repair of the aneurysm.

Yet, an additional object of the invention is to provide a procedure and system for repairing abdominal aortic aneurysms at greatly reduced cost to the patient in terms of medical expenses, rehabilitation, morbidity, and recovery time.

SUMMARY OF THE INVENTION

As illustrated in the accompanying drawings and disclosed in the accompanying claims, the invention is an aortic graft for performing an aortic anastomosis on a section of aorta, comprising, aortic graft means, having cephalic and caudal ends, and having an axis, a plurality of attachment means attached to said cephalic and caudal ends of said aortic graft means for securing said aortic graft means to the aorta, said attachment means having base means, oriented in substantially parallel relation to said axis of said aortic graft means, and attached to said aortic graft means, post means, attached to said base member and extending substantially radially away from said aortic graft means, and hook means oriented in substantially parallel relation to said axis, attached to the distal end of said post means for penetrating the aorta and securing said graft means to the aorta.

As set forth in the specification, the aortic graft of the invention is employed in a process for excluding from the circulation and, thus, rendering safe, an aortic aneurysm through the use of a balloon catheter and aortic graft comprising the steps of, inserting a contrast filled balloon catheter into the aneurysm to a proximal point just above the aneurysm abutting unaffected arterial tissue; measuring the diameter of the aorta at the proximal point just above the aneurysm; removing the contrast filled balloon catheter from the proximal point and placing it in the affected artery at a distal point just below the aneurysm abutting unaffected arterial tissue; measuring the diameter of the vessel at said distal point, just below the aneurysm; removing the contrast filled balloon catheter; measuring the distance between said proximal and distal points through radiographic techniques; inserting along with a double balloon catheter a graft having first and second ends substantially 1-4 mm larger than the size of the aorta at said proximal and distal points; blowing up the cephalic balloon from the distal end of the cephalic balloon to force hooks at the distal position of the cephalic end of said graft into mated relation with said cephalic aorta; continuing to blow up said cephalic balloon from said distal end of said cephalic balloon until said cephalic balloon is fully inflated and said proximal hooks are forced into mated relation with said artery at said proximal end of the cephalic aorta; maintaining inflation of said cephalic balloon while inflating cuadal balloon; blowing up said cuadal balloon from the proximal end of said cuadal balloon to force hooks at said proximal position of said cuadal end of said graft into mated relation with said aorta at said cuadal point; continuing to blow up said cuadal balloon from said proximal end of said cuadal balloon until said cuadal balloon is fully inflated and said distal hooks are forced into mated relation with said artery at said distal end of the caudal aorta; removing the double balloon catheter system; and inserting into said graft a first expandable ring retainer.

BRIEF DESCRIPTION OF THE DRAWINGS

The characteristics and features of the present invention will be better understood through the following detailed description and accompanying drawings which are incorporated herein by reference.

The aortic graft, and system and method of implanting an aortic graft of the present invention will now be described in further detail with reference to the drawings. The drawings and the detailed description of a preferred embodiment of the invention which follows are illustrative and explanatory only and in no way limit the scope of the invention as set forth in the appended claims.

DESCRIPTION OF A PREFERRED EMBODIMENT

Figure 1:
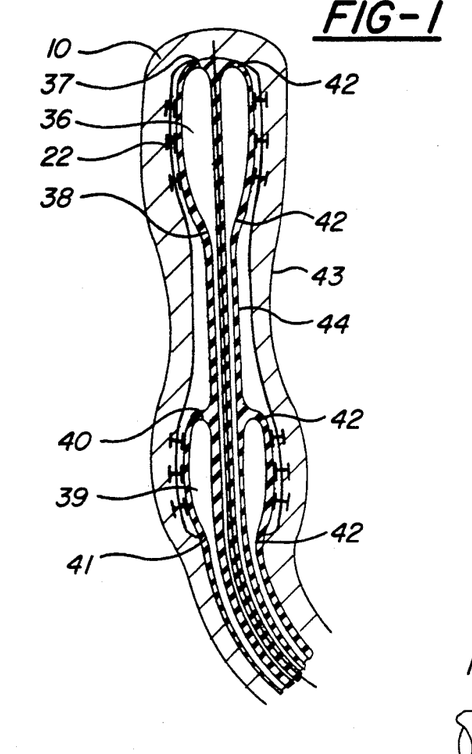
FIG. 1 is an enlarged coronal view of the aortic graft of the present invention shown with a double balloon catheter system that is used to implant it.
Figure 3:
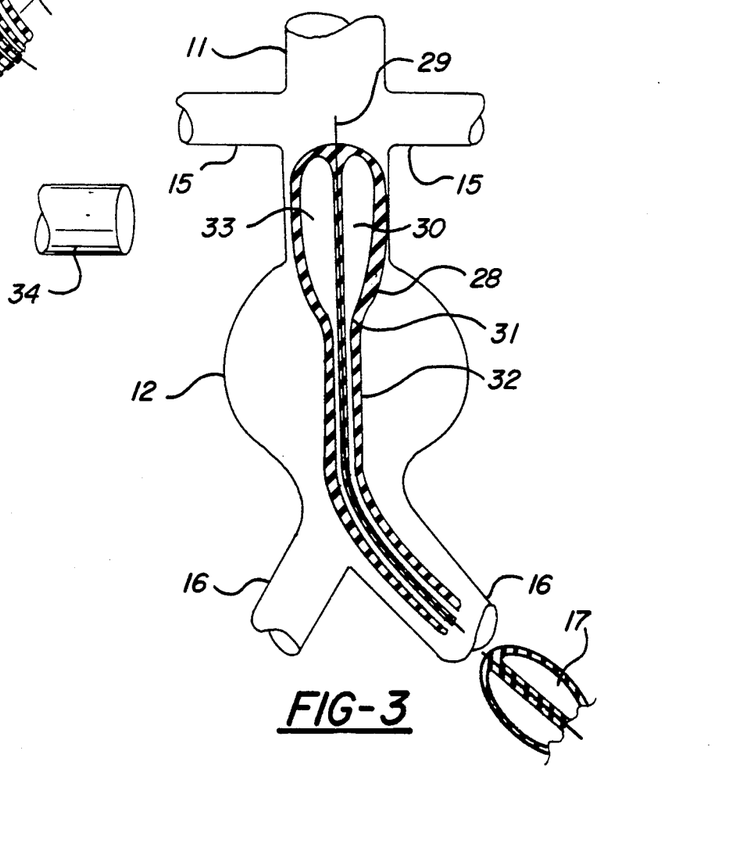
FIG. 3 is a coronal view of a balloon catheter being inserted into the cephalic end of the affected artery above the aneurysm in order to measure the diameter of the vessel.

FIG. 1 illustrates aortic graft means 10 for repairing an abdominal aortic aneurysm 12. As illustrated in FIG. 3, the aortic aneurysm 12 is located in the abdominal aorta 11 between the renal arteries 15 and the iliac arteries 16.

It will be apparent to those skilled in the art that the aortic graft 10 of the present invention can also be used in other locations without departing from the scope or spirit of the appended claims. For example, the graft could be used on any type of fluid conducting vessel such as sections of arteries located in other parts of the body or other types of vessels.

As embodied herein, aortic graft means 10 of the present invention comprises an aortic graft 18 having cephalic 19 and caudal 20 ends and a body 21. The aortic graft 18 of the present invention is preferably fabricated from a flexible, yet resilient, material such as polytetrafluoroethylene (Teflon) or other material having similar flexible and resilient properties. Other substance such as natural or synthetic polymeric substances (such as polyester fabric, Dacron, Mylar, Rayon, cellulose acetate, cellulose butynate) may also be used. A critical consideration is that the substance of which the aortic graft 18 is made be biologically inert and be compatible with the tissues into which the aortic graft is to be implanted. Many materials of this type are well known in the art.

In a preferred embodiment of the present invention aortic graft 18 has a plurality of attachment means 22 and a double balloon catheter system 35. The graft can be prepared and packaged under sterile conditions and assembled in a kit comprising first catheter system for measuring the diameter of the aorta, aortic graft 18, with attachment means 22, a second catherer system which is a double balloon catheter system 35, and a third balloon catheter system 48 with retainer rings 45. It is contemplated that the aortic graft 18, double balloon catheter system 35, and third catheter system 48 of the present invention be manufactured in various sizes so that the system of the present invention is adaptable to the size and configuration of the aortic aneurysm of the individual patient.

Figure 2:
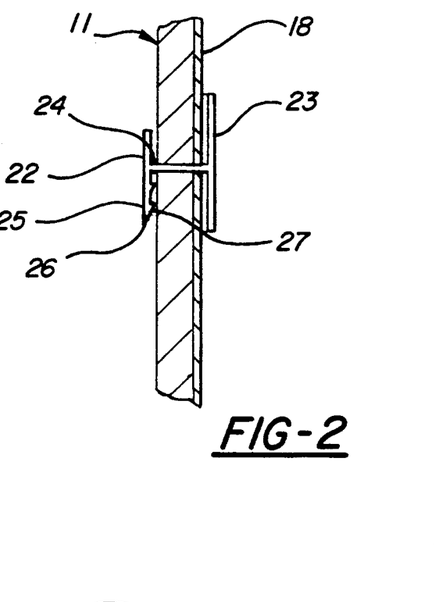
FIG. 2 is an enlarged view of an attachment means of a preferred embodiment of the present invention.

As embodied herein and shown in FIG. 2, attachment means 22 of the present invention comprises base means 23, post means 24, and hook means 25. Hook means 25, in turn, further comprises tip 26 to facilitate penetration of aorta 11 by hook 25 and barb 27 to resiliently hold attachment means in implanted position relative to aorta 11. In a preferred embodiment of the present invention, aortic graft 18, is provided with a plurality of attachment means 22, mounted in the cephalic 19 and caudal 20 ends of aortic graft 18.

In a preferred embodiment of the present invention, base means 23, is constructed of a biologically compatible material such as metal or plastic. Base 23 can be a small flat strip of metal that is oriented in substantially parallel relation to the axis of aortic graft 18. Base 23 is attached to the cephalic 19 and caudal 20 ends of aortic graft 18. This attachment can be accomplished by a variety of means including, but not limited to, gluing, welding, riveting, or simply positioning base 23 so that the distal surface of base 23 abuts the proximal surface of the lumen of aortic graft 18 and is held in place by force exerted on post 24.

Post means 24 is a post that is preferably oriented in substantially perpendicular relation to base 23. In a preferred embodiment of the present invention, post 24 is mounted on the distal surface of base 23 so that post 24 extends radially outward from the axis of aortic graft 18 when base 23 is in mounted relation to aortic graft 18. Base 23 may be secured to aortic graft 18 through a variety of means including gluing, riveting, welding, or other means that are biologically compatible and will provide a secure attachment of post 24 to base 23. Base 23 can also be secured to aortic graft 18 by mounting base 23 in the lumen of aortic graft 18 so that the distal surface of base 23 abuts the proximal surface of the lumen of aortic graft 18 so that post 24 penetrates and extends through aortic graft 18. Force exerted on the distal end of post 24 then holds base 23 and post 24 in place.

In a preferred embodiment of the present invention, hook means 25 is a hook that is mounted on the distal end of post 24. Hook 25 is oriented substantially parallel relation to base 23 and, thus, the axis of aortic graft 18 when it is implanted in aorta 11. In a preferred embodiment of the present invention, the limb of hook 25 on which tip 26 is located is longer as measured from post 23 than the end of hook 25 distal from tip 26. Further, hook 25 may have one or more barbs 27 for holding attachment means 22 and aortic graft 18 firmly in place relative to aorta 14 at the cephalic 12 and caudal 13 portions of the abdominal aorta above and below aneurysm 11 respectively.

Aortic graft means 10 is implanted in abdominal aorta 11 through the use of a double balloon catheter system 35. The double balloon catheter system 35 of the present invention, is oriented so that when the balloons are inflated, tip 26 of hook 25 engages the wall of aorta 11 in substantially non-parallel relation in order to facilitate hook 25 penetrates abdominal aorta 11 to secure aortic graft 18 of the present invention to aorta 11.

It will be apparent to those skilled in the art that various modifications and variations can be made in the construction and implantation of attachment means 22 of the present invention without departing from the scope or spirit of the claimed invention. For example, the relative lengths of the limbs of hook 25 on each side of post 24 could be modified. Post 24 in turn could assume various configurations, provided the distal end of post 24 extends radially from aortic graft 18 to penetrate through aorta 11. Hook 25 could also assume various configurations and orientations, provided it is oriented in a manner so that it does not pose a hazard to nearby organs or systems when aortic graft 18 as implanted in aorta 11. Further, attachment means 22 could be oriented so that it does not rotate in order to penetrate aorta 11 but, rather, simply erodes through aorta 11. Hence, it is intended that the present invention cover the modifications and variations of the invention, provided they come within the scope of the appended claims and their equivalents.

The operation and attachment of aortic graft means 10 can perhaps best be illustrated by the operation of the double balloon catheter system 35. Implantation of the aortic graft means of the present invention involves several steps. First, an incision is made in the femoral artery 17 or iliac artery 16 to provide a means of access to aneurysm 12. In a preferred embodiment of the present invention, as shown in FIG. 3, a first balloon catheter assembly 28 is employed to measure certain critical features of aorta 11. First balloon catheter 28, as embodied herein, comprises a guide wire 29, a balloon 30, a supply tube 31, a first balloon catheter sheath 32, and contrast material 33. Guide wire 29 is inserted through the incision in femoral artery 17 or iliac artery 16 with first catheter assembly 28. Balloon 30 is filled with a radioopaque contrast material 33 to allow visualization of balloon 30 by radiographic means. Catheter assembly 28 is threaded through the opening of femoral artery 17 or iliac artery 16 until balloon 30 of first catheter 28 has been inserted into aneurysm 12 in the abdominal aorta 11. Using a radiographic system 34, balloon 30 is aligned with the cephalic portion 13 of the abdominal aorta 11 above aneurysm 12. Balloon 30 is then inflated until it engages the interior surface of the cephalic portion 13 of abdominal aorta 11 immediately above aneurysm 12. Radiographic system 34 is then employed to measure the diameter of the abdominal aorta 11 at its cephalic portion 13, above the aneurysm. This measurement is then recorded.

Figure 4:
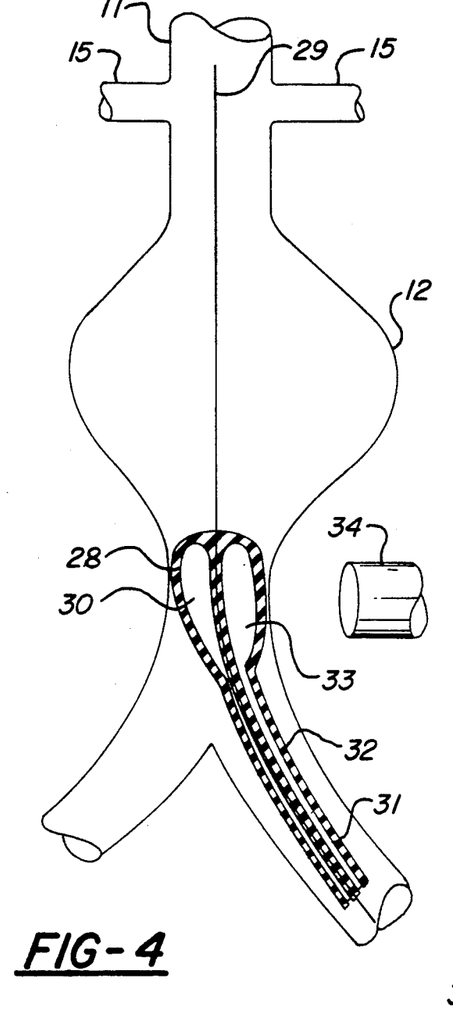
FIG. 4 is a coronal view of a contrast filled balloon catheter being inserted into the caudal end of the abdominal artery below the aneurysm to measure the diameter of the vessel.

As shown in FIG. 4, first catheter assembly 28 is then withdrawn until balloon 30 is aligned with the caudal portion 14 of abdominal aorta 11 below aneurysm 12. Balloon 30 is reinflated until it abuts the interior wall of abdominal aorta 11 at the caudal portion 14 of the abdominal aorta 11 below aneurysm 12. Radiographic system 34 is again employed to measure the diameter of abdominal aorta 11 at the caudal portion of abdominal aorta below aneurysm 12. This measurement is also recorded. Using the data collected by the radiographic system, the distance between the cephalic portion 12 of abdominal aorta 13 and the caudal portion 14 of abdominal aorta 11, above and below aneurysm 12, respectively, as well as the diameter of the cephalic and caudal regions 13 and 14 of aorta 11, are then determined. Using this information, aortic graft means 10 of appropriate size for the patient is selected.

Figure 5:
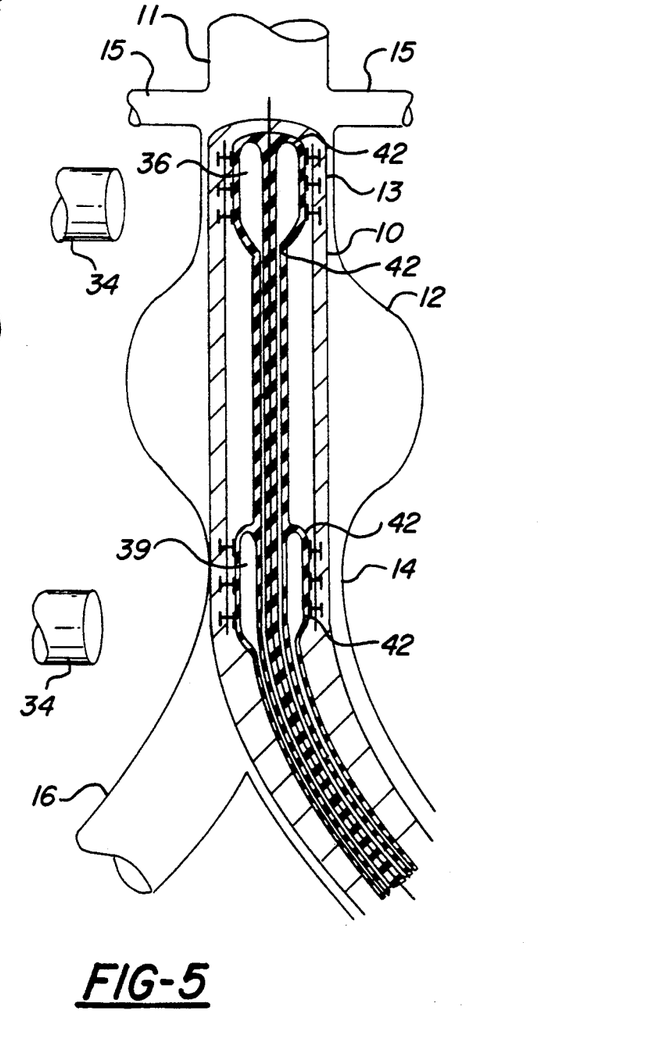
FIG. 5 is a coronal view of the aortic graft and double balloon catheter system of the present invention inserted into the abdominal artery so that the cephalic and caudal ends of the aortic graft are aligned with the cephalic and caudal portions of the aorta above and below the aneurysm, respectively.

As embodied herein aortic graft 18 is preferably 2 to 10 mm longer than the distance between the cephalic 13 and caudal 14 portions of abdominal aorta 11 as determined by the radiographic system 34. Aortic graft means 10 of the present invention comprises aortic graft 18, attachment means 22, and double balloon catheter system 35. Double balloon catheter system 35 also comprises radioopaque markers 42. Radioopaque markers 42 are provided on the proximal 37 and distal 38 ends of cephalic balloon 36 as well as on the proximal 40 and distal 41 ends of caudal balloon 39, of double balloon catheter 35. As shown in FIG. 5, using radioopaque markers 42, and radiographic system 34, aortic graft 10 is inserted through the opening in femoral artery 17 or iliac artery 16 until cephalic balloon 36 is aligned with cephalic portion 13 of abdominal aorta 11 and caudal balloon 39 is aligned with caudal portion 14 of abdominal aorta 11.

Figure 6:
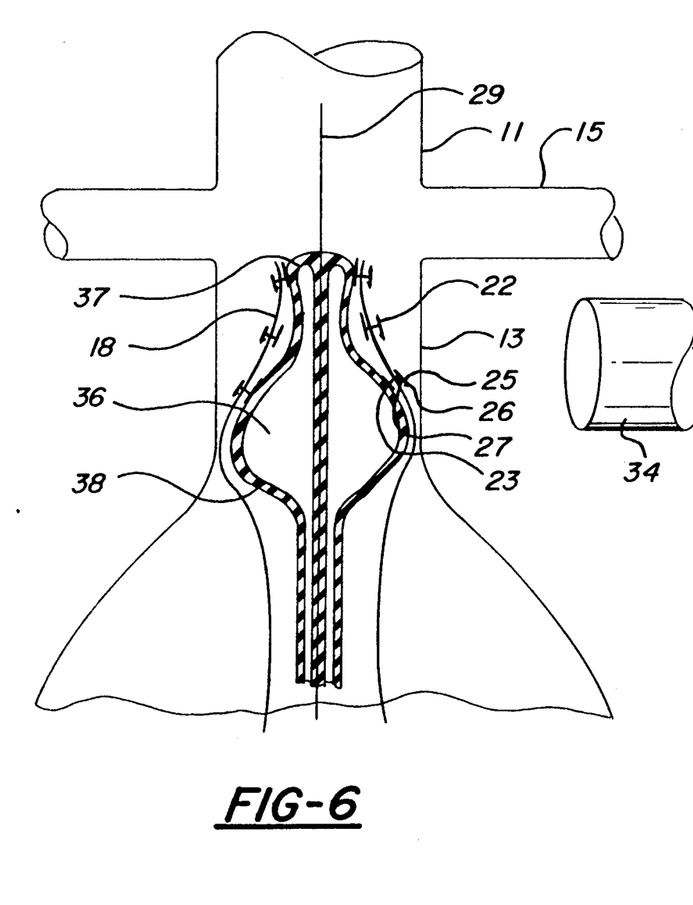
FIG. 6 is a coronal view of the cephalic abdominal aorta above the aneurysm with the aortic graft and double balloon catheter system inserted, showing the penetration of the aorta wall of the attachment means as the cephalic balloon is inflated.

Cephalic balloon 36 is then inflated. As shown in FIG. 6, inflation of cephalic balloon 36 begins at the distal end 38 of cephalic balloon 36. As distal end 38 of cephalic balloon 36 is inflated, abutting attachment means 22 rotate so that the distal ends of base 23 are moved radially outward from the axis of aortic graft 18 while the proximal ends of base 23 remain proximate to axis of aortic graft 18. This rotation orient tips 26 of hooks 25 in substantially non-parallel relation to abdominal aorta 11. As cephalic balloon 36 is inflated further, tip 26 engages abdominal aorta 11. Inflation of cephalic balloon 36 forces tip 26 to penetrate abdominal aorta wall 11 so that hook 25 extends through abdominal aorta wall 11. Barb 27 passes through the penetration so that tip 26 and barb 27 of hook 25 penetrate abdominal aorta wall 11 and lie on the outer wall surface of abdominal aorta 11.

Figure 7:
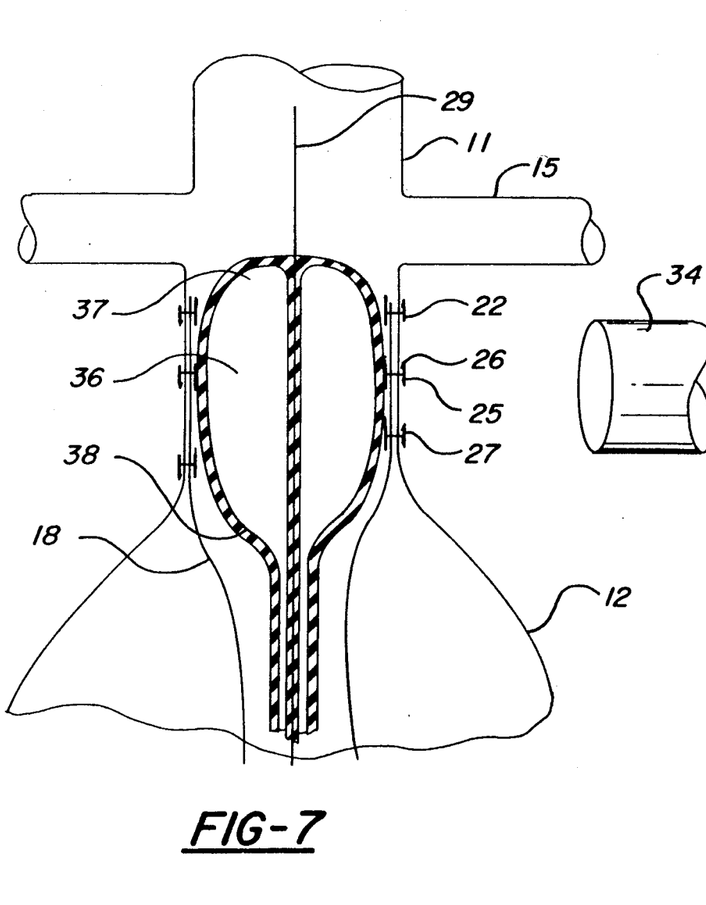
FIG. 7 is a coronal view of the aortic graft and cephalic balloon of FIG. 6 shown at a subsequent stage during inflation of the cephalic balloon as attachment means have penetrated the aorta wall.

As shown in FIG. 7, inflation of cephalic balloon 36 continues in this manner, forcing attachment means 22 through abdominal aorta wall 11 until cephalic balloon 36 is fully inflated. When cephalic balloon 36 is fully inflated, attachment means 22 on cephalic portion 19 of aortic graft 18 will penetrate abdominal aorta wall 11 at cephalic region 13, firmly and permanently anchoring aortic graft 18 to abdominal aorta 11. Cephalic balloon 36 is fully inflated and attachment means 22 and cephalic portion 19 of aortic graft 18 are anchored in proximal portion 13 of vessel wall 11, cephalic balloon is left fully distended. The distention of cephalic balloon 36 effectively closes off the flow of blood through abdominal aorta 11 during the remainder of the procedure. Inflation of cephalic balloon 36 firmly holds the cephalic portion 19 of aortic graft 18 in place while the caudal portion 20 of aortic graft 18 is being implanted in the caudal portion 14 of abdominal aorta 11.

Figure 8:
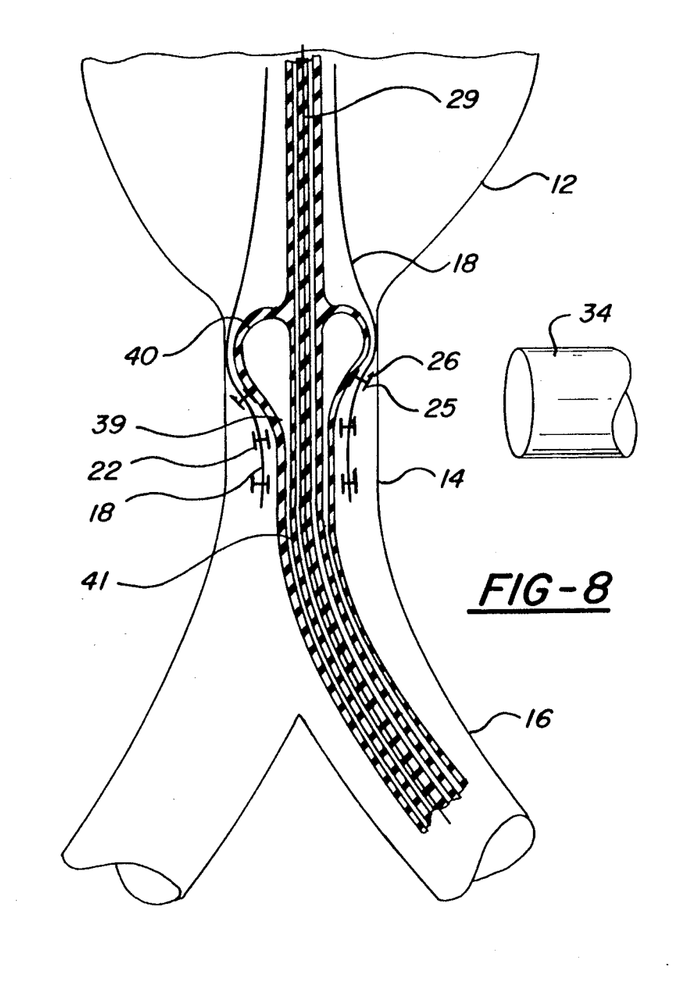
FIG. 8 is a coronal view of the caudal abdominal aorta below the aneurysm with the aortic graft and double balloon catheter system inserted, showing the penetration of the aorta wall of the attachment means as the caudal balloon is inflated.
Figure 9:
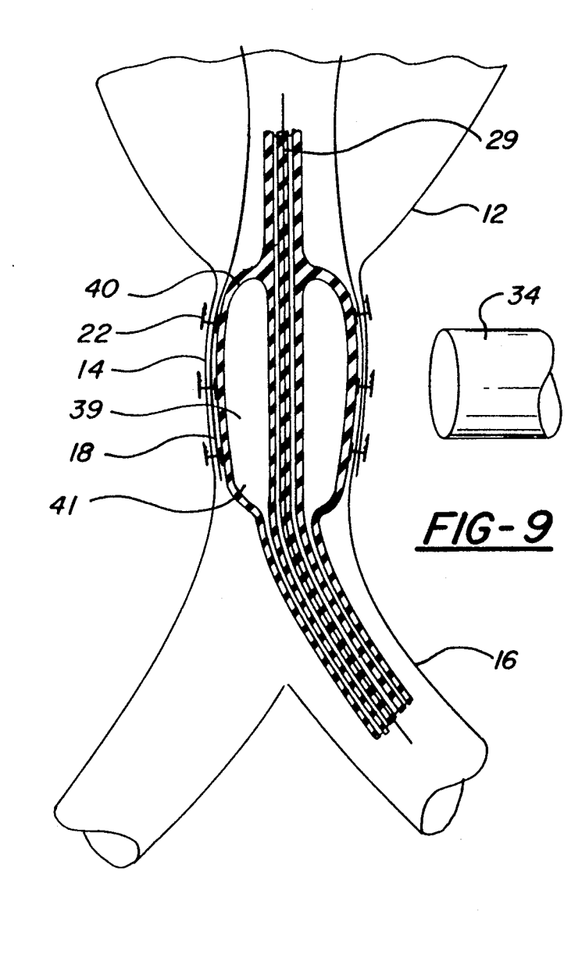
FIG. 9 is a coronal view of the aortic graft and cephalic balloon of FIG. 8 shown at a subsequent stage during inflation of the caudal balloon as attachment means have penetrated the aorta wall.

As shown in FIG. 8, caudal portion 20 of aortic graft 18 is implanted in caudal portion 14 of abdominal aorta 11 by inflating caudal balloon 39 of double balloon system 35 beginning at the proximal end 40 of caudal balloon 39. As proximal end 40 of caudal balloon 39 is inflated, attachment means 22 in caudal portion 20 of aortic graft 18 rotate as described above with respect to cephalic end 19 so that attachment means 22 of caudal portion of aortic graft 18 are firmly and permanently mounted in caudal portion 14 of abdominal aorta 11, as shown in FIG. 9.

Figure 10:
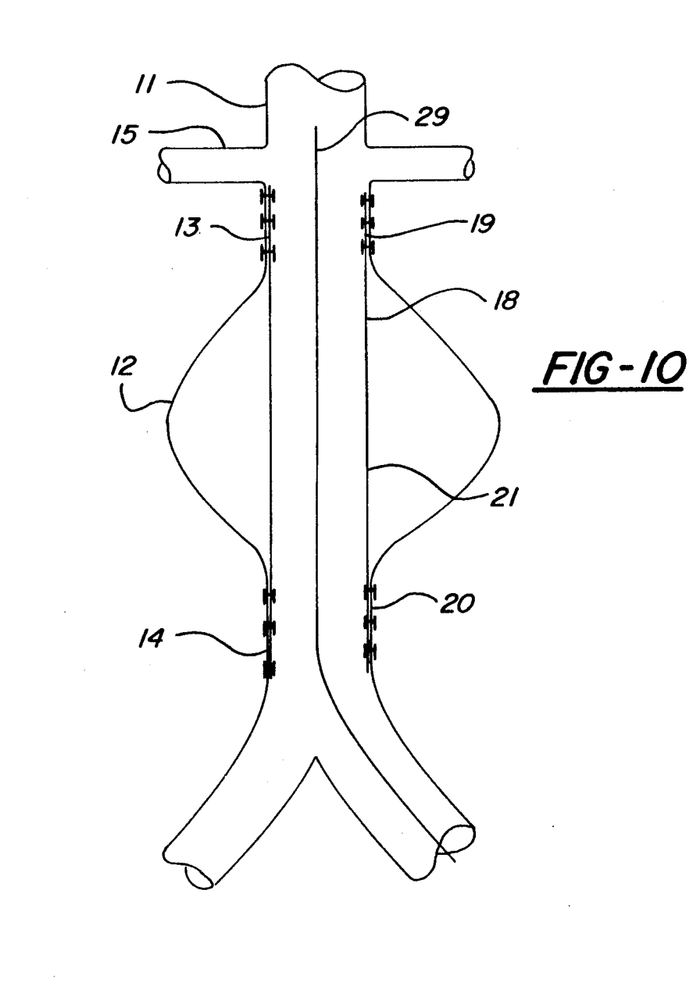
FIG. 10 is a coronal view of the aortic graft of the present invention after attachment means of cephalic and caudal ends have been implanted in the aorta wall and the double balloon catheter system has been withdrawn, excluding the aneurysm.

As shown in FIG. 10, once cephalic balloon 36 and caudal balloon 39 are fully distended, aortic graft 18 is seated both proximally and distally in abdominal aorta 11. At that point, cephalic 19 and caudal 20 portions of aortic graft 18 effectively exclude further blood from the proximal or distal aorta from reaching aneurysm 11. Body 21 of aortic graft 18 functions as abdominal aorta wall 11 of aneurysm 12. As shown in FIG. 10, once aortic graft 18 is fully seated in cephalic 13 and caudal 14 portions of abdominal aorta 11, double balloon catheter system 35 is removed. Aortic graft 18 then assumes the full pressure and stress of the circulatory flow through abdominal aorta 11 effectively excluding aneurysm 12 and, thereby, substantially relieving aneurysm 12 of the stresses on it.

Figure 11:
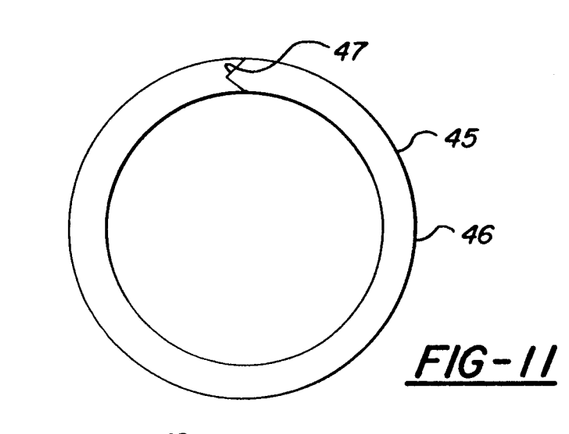
FIG. 11 is a top view of a retainer ring of the present invention.

In a preferred embodiment of the present invention, aortic graft means 10 further comprises retainer means 45. Retainer means 45 can be a resilient ring of material which functions to hold aortic graft 18 firmly in place in abdominal aorta 11. As embodied herein, retainer 45 comprises body 46, locking means 47. In a preferred embodiment of the invention, as shown in FIG. 11, retainer 45 can be a split ring which is configured so that the two ends of the split ring cooperate to form a smooth ring. Retainer means 45 prevents blood from seeping into the aneurysm between the aortic wall and the graft by placing the graft in compression between retainer means 45 and the aortic wall, obliterating the potential space between the graft and the aortic wall.

Figure 12:
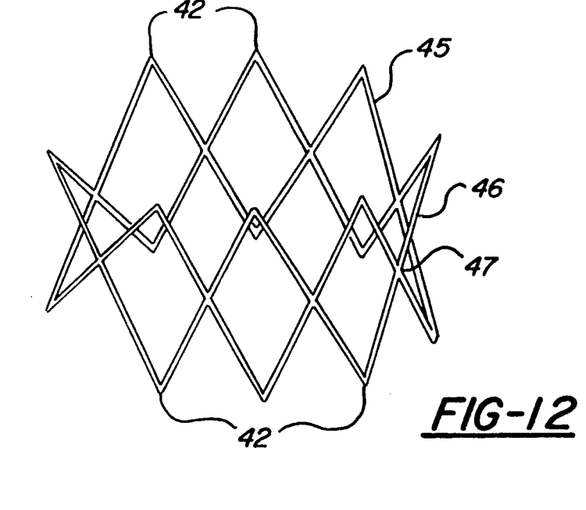
FIG. 12 is an oblique view of an alternative form of the retainer ring of the present invention.

It will be apparent to those skilled in the art that various modifications and variations can be made in the construction and implantation of attachment means 22 of the present invention without departing from the scope or spirit of the claimed invention. For example, retiner 45 can be a resilient mesh web as shown in FIG. 12. Body 46 of the web preferably comprises legs which are mounted in relation to each other so that the web can collapse to allow for for insertion and to lock in place once it has been implanted and expanded. Alternatively retainer 45 comprises a series of short resilient segments which ratchet past one another resiliently to maintain the diameter of said retainer ring against compression. Hence, it is intended that the present invention cover the modifications and variations of the invention, provided they come within the scope of the appended claims and their equivalents.

Figure 13:
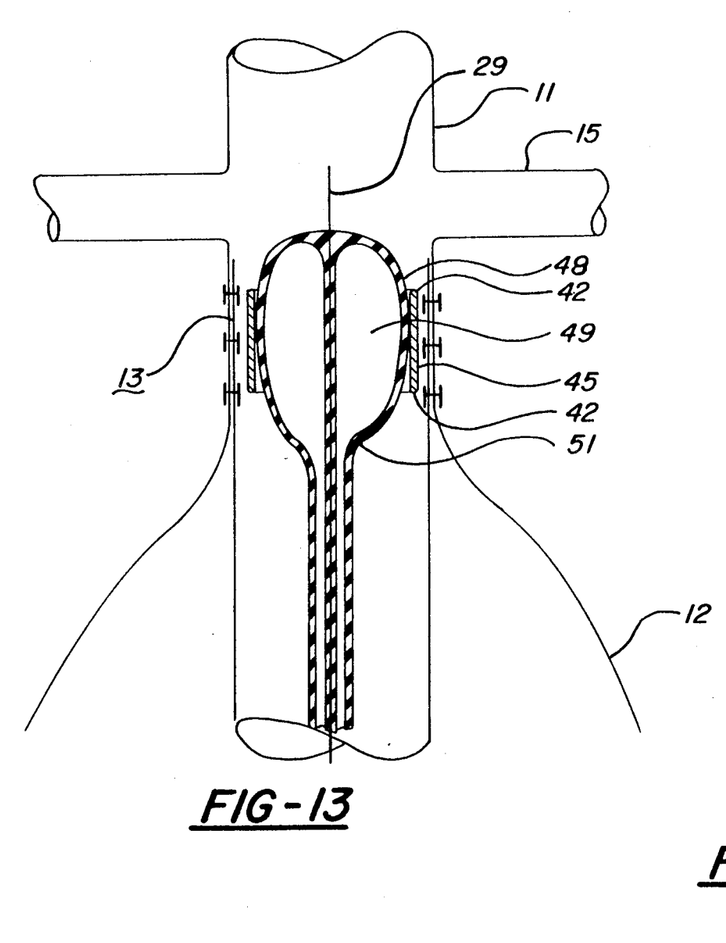
FIG. 13 is a coronal view of the cephalic end of aortic graft of the present invention showing installation of retainer ring in cephalic end with a balloon catheter.

As shown in FIG. 10, after double balloon catheter 35 is removed from abdominal aorta 11, guide wire 29 is left in place. As shown in FIG. 13, retainer 45 is inserted into abdominal aorta 11 through the use of third catheter system 48. Retainer 45 has radioopaque markers 42 on its proximal and distal surfaces. As retainer 45 and third catheter assembly 48 are inserted into abdominal aorta 11, radiographic system 34 tracks the location of retainer 45 relative to cephalic portion 13 and 19 of the abdominal aorta 14 and aortic graft 18, respectively. Once retainer 45 has been aligned with cephalic portion 12 and 19 of abdominal aorta 14 and aortic graft 18, respectively, cephalic balloon 49 is inflated. As cephalic balloon 49 is distended, locking means 47 engage, fixing retainer 45 in the aorta 11 the open position. Once balloon 30 has been fully inflated so that retainer 45 is fully expanded, retainer 45 distends aortic graft 18 and aorta 11, forcing aortic graft 18 and attachment means 22 against cephalic portion 13 of abdominal aorta 11.

Figure 14:
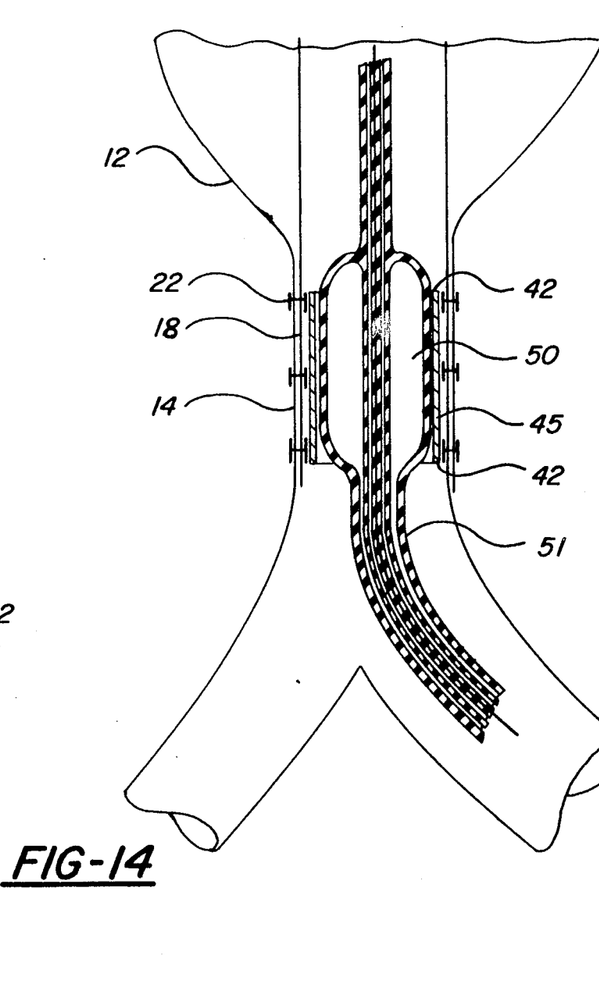
FIG. 14 is a coronal view of the caudal end of aortic graft of the present invention showing installation of retainer ring in caudal end with a balloon catheter.
Figure 15:
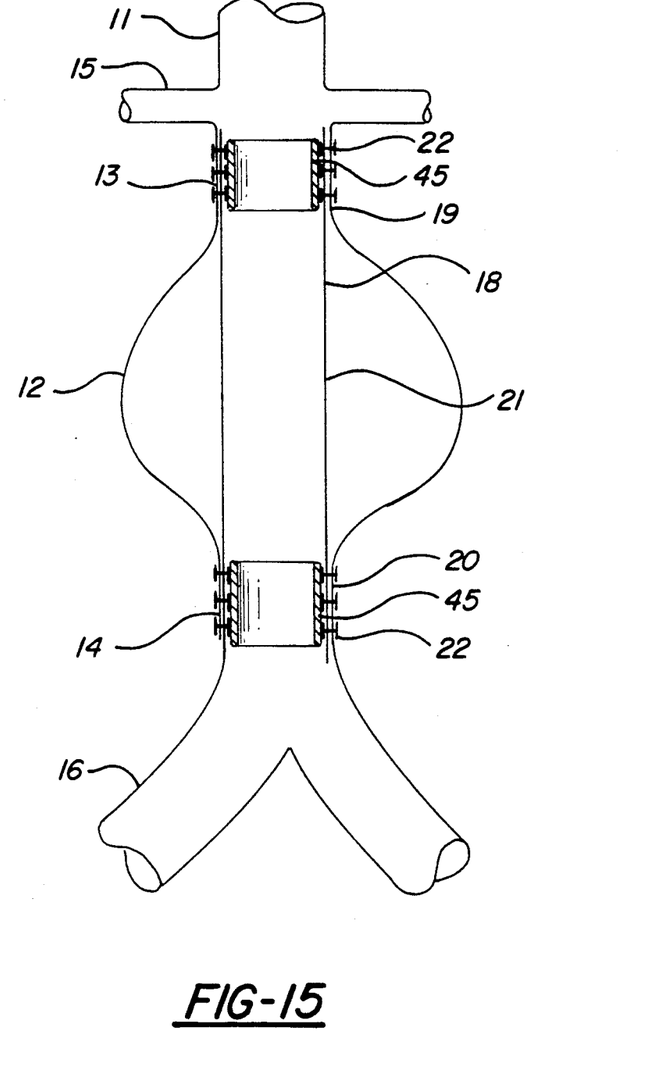
FIG. 15 is a coronal view of the aortic graft of the present invention showing the graft implanted in the aorta excluding the aortic aneurysm.

As shown in FIG. 14, caudal balloon 50 is then inflated, locking retainer 45 in the caudal portion of aortic graft 20 and aorta 14. Third catheter system 48 is then removed, along with guide wire 29. The incision in femoral artery 17 or iliac artery 16, through which the procedure was performed, is then closed and sutured. Circulation to the lower limbs is restored with aortic graft 18 excluding aneurysm 12 from circulation.

It will be apparent to those skilled in the art that various modifications and variations of the invention can be made without departing from the scope or spirit of the appended claims. In particular, aortic graft means 10 can be used with or without retainer 45. Retainer 45 could assume a variety of configurations, shapes and sizes while performing the function of securing aortic graft means 10 and abdominal aorta 14. Attachment means 22 could also assume a variety of configurations in accordance with the scope and spirit of the appended claims. Moreover, the direction in which each of the balloons of the double balloon catheter system 35 is inflated is not critical, provided attachment means 22 is oriented relative to the direction of inflation of cephalic 36 and caudal 39 balloons to facilitate penetration of aorta 11. Hence, it is intended that the present invention cover the modifications and variations of the invention, provided they come within the scope of the appended claims or their equivalents.

I claim:

1. An aortic graft for performing an aortic anastomosis on a section of aorta, comprising, flexible aortic graft means, having cephalic and caudal ends, and having axial axis and radial direction,
    a plurality of attachment means attached to said cephalic and caudal ends of said aortic graft means for securing said aortic graft means to the aorta, each of said attachment means having base means, oriented in substantially parallel relation to said axis of said aortic graft means, and attached to said aortic graft means,
    post means, attached to said base means, extending radially away from said aortic graft means, and orientated in substantially perpendicular relation to said axis,
    hook means oriented in substantially parallel relation to said axis, mounted to the distal end of said post means for penetrating the aorta and securing said graft means to the aorta,
    wherein said attachment means places said aortic graft means in circumferential apposition to the aorta to prevent substantial leakage between said aortic graft means and the aorta.

2. The aortic graft of claim 1, wherein said aortic graft means is subtantially cylindrical in shape.

3. The aortic graft of claim 1, wherein said aortic graft means comprises a resilient flexible material.

4. The aortic graft of claim 1, wherein said aortic graft means comprises a material inert to bodily fluids.

5. The aortic graft of claim 1, wherein said hook means further comprises barbed hooks.

6. The aortic graft of claim 1, wherein said aortic graft means further comprises retainer means for maintaining said cephalic and caudal ends of said aortic graft in mated relation with abutting portions of the aorta.

7. An aortic graft, adapted to be implanted by means of a balloon catheter for performing an aortic anastomosis on a section of abdominal aorta, comprising, substantially cylindrical flexible aortic graft means, having first and second ends,
    a plurality of attachment means attached to said first and second ends of said aortic graft means for securing said aortic graft means to the aorta,
    each of said attachment means having
        a base member attached to said aortic graft means at one of said first or second ends thereof, oriented in substantially parallel relation to the axial axis of said aortic graft means,
        post means, attached in substantially perpendicular relation to said base member and extending radially from said aortic graft means,
        hook means attached to the distal end of said post means for penetrating the aorta and securing said graft means to the aorta,
    said hook means further comprising a barbed hook,
    wherein said attachment means places said aortic graft means in circumferential apposition to the aorta to prevent substantial leakage between said aortic graft means and the aorta, and
    wherein said aortic graft is adapted to be implanted by use of said balloon catheter means.

8. The aortic graft of claim 7, wherein said aortic graft means comprises a resilient flexible material.

9. The aortic graft of claim 7, wherein said aortic graft means comprises a material inert to bodily fluids.

10. The aortic graft of claim 7, wherein said aortic graft means further comprises retainer means for maintaining said first and second ends in mated relation with adjoining portions of the aorta.

11. An aortic graft, adapted to be implanted by means of a balloon catheter, for performing an aortic anastomosis on a section of abdominal aorta, comprising, substantially cylindrical, flexible, aortic graft means, having first and second ends and having axial and radial directions, a plurality of attachment means disposed at said first and second ends of said aortic graft means for securing said aortic graft means to the aorta, each of said attachment means having a base member abutting a surface of said aortic graft at one of said first or second ends of said aortic graft, said base member oriented in substantially parallel relation to the longitudinal axis of said aortic graft, post means, attached in substantially perpendicular relation to said base member and extending through one of said first or second ends of said aortic graft radially from said aortic graft, hook means, attached to the distal end of said post means for penetrating the aorta and securing said aortic graft to the aorta, said hook means further comprising at least one barb, retainer means for maintaining said first and second ends of said aortic graft means in mated relation with adjoining portions of the aorta, wherein said attachment means and said retainer means cooperate to place said aortic graft means in circumferential apposition to the aorta to prevent substantial leakage between said aortic graft and the aorta, and wherein said aortic graft is adapted to be implanted in the aorta by use of said ballon catheter means.

12. The aortic graft of claim 11, wherein said aortic graft means comprises a resilient flexible material.

13. The aortic graft of claim 11, wherein said retainer means is in the form of a ring, and comprises a series of short segments which ratchet past one another to resiliently maintain the diameter of said retainer means.

14. A process for repairing an aortic aneurysm through the use of a ballon catheter and aortic graft comprising the steps of, inserting a contrast filled ballon catheter into the aneurysm to a cephalic point, just above the aneurysm abutting unaffected arterial tissue;

measuring to diameter and position of the aorta at the cephalic point, just above the aneurysm;

withdrawing the contrast filled ballon catheter system from said cephalic point;

repositioning the contrast filled balloon catheter in the affected artery to a caudal point, below the aneurysm abutting unaffected arterial tissue;

reinflating the contrast filled balloon;

measuring to diameter and position of the aorta at said distal point, just below the aneurysm;

removing the contrast filled balloon catheter;

measuring the distance between said cephalic and caudal points through radiographic techniques;

inserting along with a double ballon catheter a graft having first and second ends substantially 1–10 mm larger than the size of the aorta at said cephalic and cuadal points;

inflating the cephalic balloon from the distal end of the cephalic balloon to force hooks at the distal postion of the proximal end of said graft into mated relation with said cephalic aorta;

continuing to blow up said cephalic balloon from said distal end of said cephalic balloon until said cephalic balloon is fully inflated and said proximal hooks are forced into mated relation with said artery at said cephalic point;

maintaining inflation of said cephalic balloon while inflating caudal balloon;

inflating said caudal balloon from the proximal end of said caudal balloon to force hooks at said proximal position of said caudal end of said graft into mated relation with said aorta at said caudal point;

continuing to inflate said caudal balloon from said proximal end of said caudal balloon until said caudal balloon is fully inflated and said caudal hooks are forced into mated relation with said artery at said caudal point;

removing the double balloon catheter system;

inserting into said graft one or more retainers and a third balloon catheter system;

implanting retainers at said cephalic and caudal positions inside aortic said graft;

removing all catheters and wires;

repairing all arterial incisions; and closing incision used to access femoral or iliac artery.

15. The aortic graft of claim 11, wherein said retainer means is a resilient mesh web.

16. The aortic graft of claim 11, wherein each said hook means is substantially parallel to the base member, and where the barbs are oriented towards the base member and away from the aorta.

17. The aortic graft of claim 11, wherein said hook means has a first and second tip, where the barb is located on said first tip, wherein said first tip is longer than said second tip, as measured from said post means.

* * * * *